(12) United States Patent
Uckun

(10) Patent No.: US 6,589,992 B2
(45) Date of Patent: Jul. 8, 2003

(54) INHIBITING COLLAGEN-INDUCED PLATELET AGGREGATION

(75) Inventor: Fatih M. Uckun, White Bear Lake, MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

(21) Appl. No.: 10/077,514

(22) Filed: Feb. 15, 2002

(65) Prior Publication Data

US 2002/0169207 A1 Nov. 14, 2002

Related U.S. Application Data

(63) Continuation of application No. PCT/US00/42370, filed on Nov. 29, 2000.
(60) Provisional application No. 60/269,094, filed on Feb. 15, 2001, and provisional application No. 60/168,103, filed on Nov. 30, 1999.

(51) Int. Cl.$^7$ .............................................. A61K 31/167
(52) U.S. Cl. ....................................... 514/626; 514/627
(58) Field of Search ................................... 514/626, 627

(56) References Cited

U.S. PATENT DOCUMENTS

| | | | |
|---|---|---|---|
| 4,559,157 A | 12/1985 | Smith et al. ................... | 252/90 |
| 4,608,392 A | 8/1986 | Jacquet et al. ............... | 514/844 |
| 4,820,508 A | 4/1989 | Wortzman .................... | 424/59 |
| 4,938,949 A | 7/1990 | Borch et al. .................. | 424/10 |
| 4,992,478 A | 2/1991 | Geria .......................... | 514/782 |
| 5,399,346 A | 3/1995 | Anderson et al. ......... | 424/93.21 |
| 5,968,902 A | 10/1999 | Scarborough et al. ......... | 514/9 |
| 5,972,967 A | 10/1999 | Gelotte ....................... | 514/331 |

FOREIGN PATENT DOCUMENTS

| | | |
|---|---|---|
| EP | 0607775 | 7/1994 |
| EP | 0652214 | 5/1995 |
| EP | 0821952 | 2/1998 |
| WO | 9954286 | 10/1999 |
| WO | 0056737 | 9/2000 |

OTHER PUBLICATIONS

Rawlings, et al., "Bruton's Tyrosin Kinase is a Key Regulator in B–Cell Development", *Immunological Reviews*, No. 138, pp. 105–119 (Apr. 1994).

Kurosaki, T., "Molecular mechanisms in B cell antigen receptor signaling",*Current Opinion in Immunology*, vol. 9, No. 3, pp. 309–318 (Jun. 1997).

Uckun, F.M., 1998, "Bruton's Tyrosine Kinase (BTK) as a Dual–Function Regulartor of Apoptosis", *Biochemical Pharmacology*, vol. 56, 683–691.

Swinyard E., et al., "Topical Drugs", *Remington's Pharmaceutical Sciences, Remington's Practice of Pharmacy*, Chap. 43, pp. 763–786, (1980).

Tibbles H. E., et al., "Inhibition Of Collagen–Induced Aggregation By Selectively Targeting Bruton's Tyrosine Kinase With LFM–A13", *Blood*, vol. 94, No. Suppl. 1, Part 1 (Nov. 15, 1999) p. 221a.

Mahajan S., et al., "Rational Design And Synthesis of a Novel Anit–Leukemic Agent Targeting Bruton's Tyrosine Kinase (BTK), LFM–A13 Ualpha–Cyano–Beta–Hydroxy–Bet A–Methyl–N . . . ",*Journal of Biological Chemistry*, vol. 274, No. 14 (Apr. 2, 1999) p. 9588, col. 1, paragraph 3, p. 9597, col. 2, paragraph 2.

Tibbles Heather E., et al., "Prevention of fatal thromboembolism in mice by selectively targeting BTK and TEC kinases in platelets with alph–cyano–beta–hydroxy–beta–m ethyl–N . . . ", *Blood*, vol. 96, No. 11, Part 1 (Nov. 16, 2000) p. 275a.

*Primary Examiner*—Phyllis G. Spivack
(74) *Attorney, Agent, or Firm*—Merchant & Gould P.C.

(57) ABSTRACT

The present invention describes a therapeutic method useful for treating or preventing a condition of platelet aggregation in a subject including administering to the subject a pharmaceutically effective amount of a compound or composition that inhibits BTK and collagen-induced platelet aggregation. The condition of platelet aggregation includes cardiovascular, hematopoietic and cerebrovascular diseases.

11 Claims, 10 Drawing Sheets

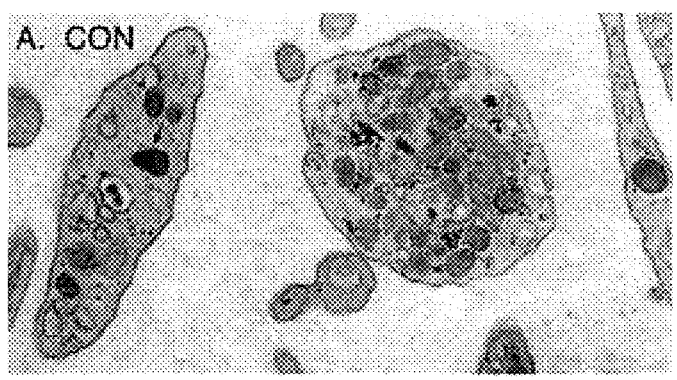
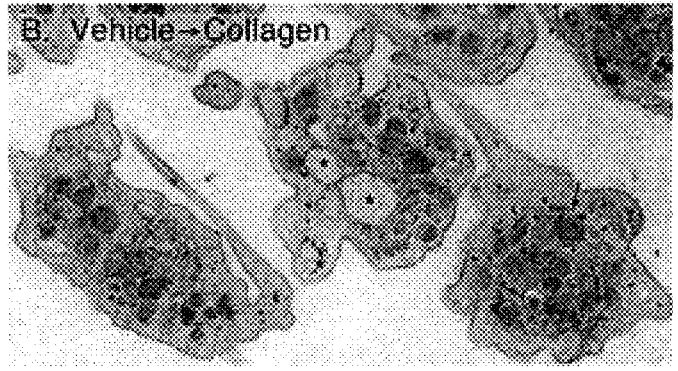
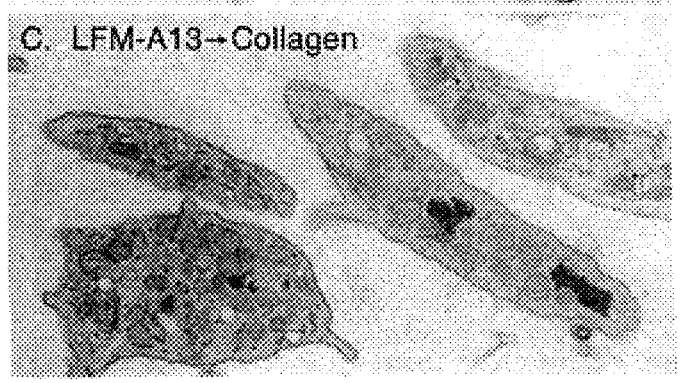
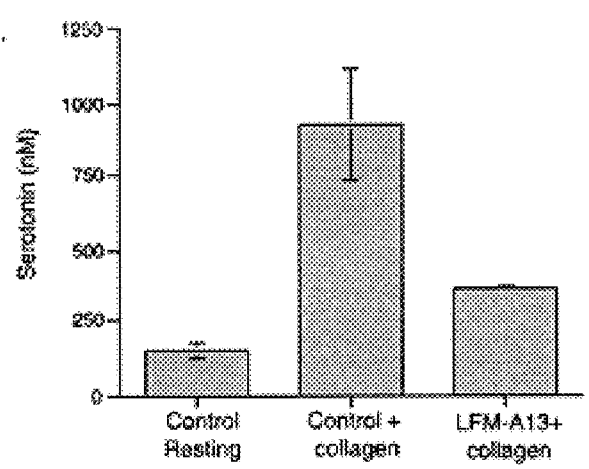

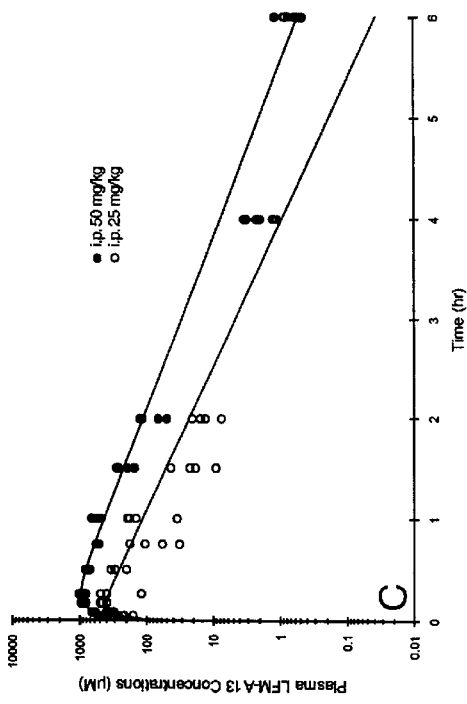
Fig. 7A
| Dose (mg/kg) | $V_c^a$ (ml/kg) | $CL_s^a$ (ml/h/kg) | AUC (μM·h) | $C_{max}$ (μM) | $t_{1/2}$ (min) | $t_{max}$ (min) |
|---|---|---|---|---|---|---|
| i.v., 25 | 95 (95 ± 3) | 186 (184 ± 14) | 374 (384 ± 30) | 729 (731 ± 22) | 45 (44 ± 4) | ND |
| i.p., 10 | 198 (184 ± 3) | 443 (445 ± 20) | 63 (63 ± 3) | 90 (94 ± 8) | 19 (17 ± 1) | 12 (12 ± 2) |
| i.p., 20 | 169 (159 ± 16) | 308 (309 ± 21) | 181 (183 ± 14) | 236 (243 ± 16) | 23 (22 ± 1) | 11 (12 ± 1) |
| i.p., 25 | 138 (144 ± 18) | 221 (234 ± 29) | 314 (308 ± 31) | 388 (383 ± 35) | 26 (26 ± 1) | 10 (10 ± 1) |
| i.p., 40 | 120 (111 ± 7) | 165 (172 ± 12) | 672 (653 ± 47) | 630 (640 ± 44) | 30 (27 ± 1) | 17 (18 ± 1) |
| i.p., 50 | 102 (103 ± 4) | 136 (136 ± 4) | 1018 (1023 ± 31) | 946 (940 ± 16) | 31 (32 ± 1) | 16 (16 ± 1) |
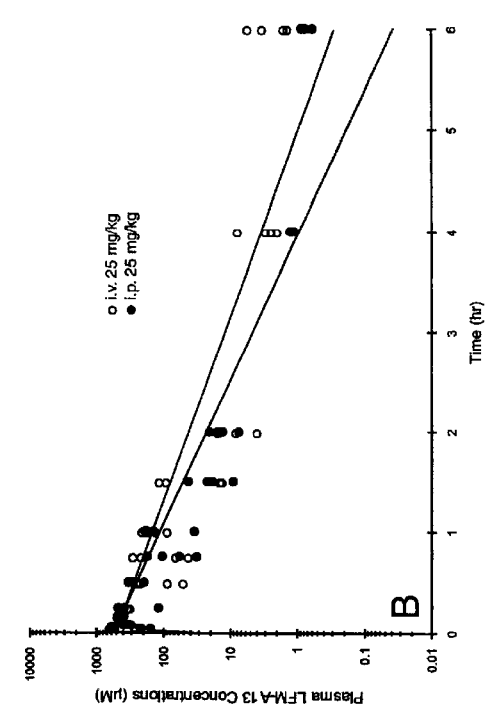
Fig. 7B
Fig. 7C

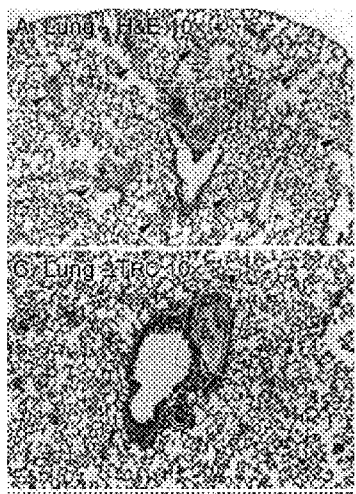
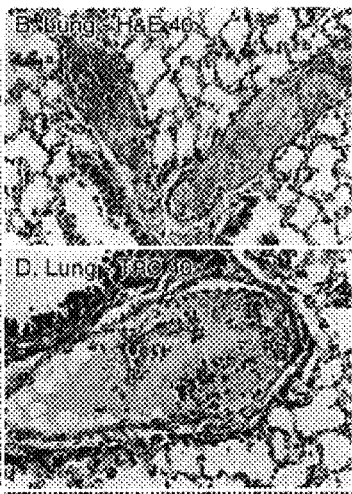
Fig. 8A  Fig. 8B
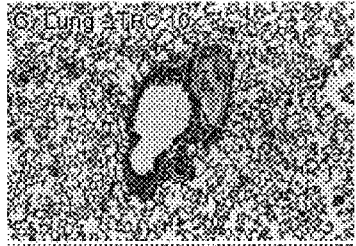
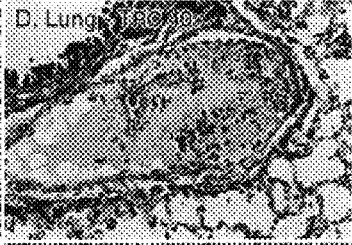
Fig. 8C  Fig. 8D
Fig. 8E  Fig. 8F
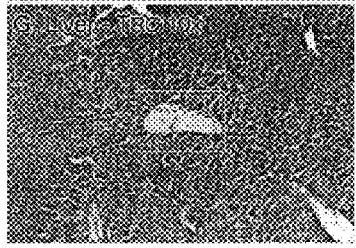
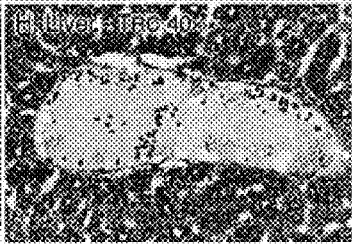
Fig. 8G  Fig. 8H Time Following Thrombopiastin Administration (Minutes)

B. Life Table Analysis

| Treatment Group | # of Mice | Proportion Surviving (%) | | | Median EFS | P-value |
| --- | --- | --- | --- | --- | --- | --- |
| | | 3 min. | 6 min. | 48 hr. | | |
| DMSO Control | 20 | 32 ± 11 | 5 ± 5 | 0 ± 0 | 2.5 min | |
| Warfarin 3 mg/kg | 10 | 80 ± 13 | 30 ± 15 | 10 ± 9 | 5.3 min | 0.169 |
| LFM-A13 20 mg/kg x 2 | 10 | 60 ± 16 | 60 ± 16 | 20 ± 13 | 8.0 min | 0.044 |
| LFM-A13 40 mg/kg x 2 | 10 | 90 ± 10 | 80 ± 13 | 80 ± 13 | >48 hr. | <0.001 |

A. Collagen 20 min. (5 µg/ml)

D. Collagen 24 hrs. (5 µg/ml)

B. Collagen 20 min. (2 µg/ml)

E. Collagen 24 hrs. (2 µg/ml)

C. αThrombin 20 min. (0.1 U/ml)

F. αThrombin 24 hrs. (0.1 U/ml)

INHIBITING COLLAGEN-INDUCED PLATELET AGGREGATION

PRIORITY

This application is a continuation under 35 USC §111 of international application number PCT/US00/42370, which was filed on Nov. 29, 2000 claiming priority under 35 U.S.C. §119 (a)-(e) to U.S. Provisional Application No. 60/168,103 filed on Nov. 30, 1999. The international application was published under PCT Article 21(2) in English as WO 01/41754. This continuation application also claims priority under 35 U.S.C. §119(e) to U.S. Provisional Application No. 60/269,094, filed Feb. 15, 2001.

TECHNICAL FIELD

The present invention relates to treating or preventing a disease or condition involving platelet aggregation. The method includes administering a pharmaceutically effective amount of a compound that inhibits platelet aggregation and more particularly inhibits collagen-induced platelet aggregation.

BACKGROUND

Heart disease, a common cause of death in today's society, is often a result of ischemic and/or thromboembolic events or syndromes including myocardial infarction, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts and other cardiovascular devices. These events and syndromes represent a variety of stenotic and occlusive vascular disorders involving platelet aggregation on vessel walls or within the lumen.

The basic mechanism of platelet aggregation has been well studied. The mechanism starts with a blood vessel injury such as narrowing of the lumen, plaque formation, or the presence of foreign bodies/medical instruments. This injury leads to platelet activation and binding of fibrinogen and ligands.

Platelet binding via the surface $\alpha_2\beta_1$ integrin and glycoproteins GPVI to the extracellular matrix protein collagen from exposed subendothelium at sites of vascular injury initiates a tyrosine kinase-dependent signal transduction cascade leading to platelet activation, degranulation, aggregation, and formation of a hemostatic thrombus (Gibbins et al., (1997) *FEBS Lett,* 413:255-91; Moroi, M. and Jung, S. M., (1997) *Thromb Haemost* 78:439-444; Quek, et al. (1998) *Curr Biol,* 8:1137-1140; Tsuji, et al., (1997) *J Biol Chem* 272:23528-23531).

Bruton's tyrosine kinase (BTK), a member of the BTK/Tec family of protein tyrosine kinases (PTKs), is a cytoplasmic PTK involved in signal transduction pathways regulating growth and differentiation of B-lineage lymphoid cells (Rawlings, D. J., and Witte, O. N. (1994) *Immunol. Rev.* 138, 105-119; Kurosaki, T. (1997) *Curr Opin. Immunol.* 9, 309-318; and Uckun, F. M. (1998) *Biochemical Pharmacology,* et al., 56, 683-691). BTK participates in signal transduction pathways initiated by the binding of a variety of extracellular ligands to their cell surface receptors. Following ligand binding of B cell antigen receptors (BCR), BTK activation by the concerted actions of the PTKs Lyn and Syk (Kurosaki, T. (1997) *Curr Opin. Immunol.* 9, 309-318) is required for induction of phospholipase C-γ2 mediated calcium mobilization (Kurosaki, T. (1997) *Curr Opin. Immunol.* 9, 309-318).

BTK participates in the collagen receptor glycoprotein VI (GP VI)-Fc receptor gamma (FcRγ) chain coupled signaling. Tyrosine phosphorylation of the immune-receptor tyrosine based activation motif (ITAM) of the FcRγ chain leads to phosphorylation and activation of phospholipase C gamma 2 (PLCγ2). Activated PLCγ2 converts PI-4,5-bisphospate ($PIP_2$) to inositol triphosphate ($IP_3$), leading to intracellular calcium mobilization.

Gelotte, U.S. Pat. No. 5,972,967 and Scarborough, et al. U.S. Pat. No. 5,968,902 have described certain compounds and compositions that inhibit binding to a platelet by limiting the binding of fibrinogen. Nevertheless, there still is a need for finding compounds and improved methods to treat or prevent a condition of platelet aggregation.

SUMMARY

In accordance with the purpose(s) of this invention, as embodied and broadly described herein, this invention, in one aspect, relates to a method for inhibiting platelet aggregation by administering an effective amount of a compound of the formula:

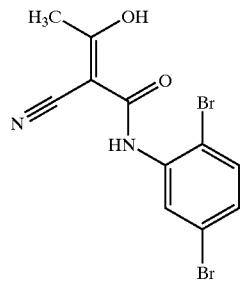

or a pharmaceutically acceptable acid addition salt thereof.

In a second aspect, the invention relates to a method of preventing or treating a disease or condition involving platelet aggregation in a subject comprising administering to a subject an effective amount of a compound of the formula:

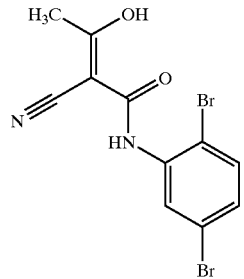

or a pharmaceutically acceptable acid addition salt thereof.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings that are incorporated in and constitute a part of this specification illustrate several experimental examples and together with the description, serve to explain the principles of the invention.

BRIEF DESCRIPTION OF THE DRAWINGS

FIGS. 4A-4D show Transmission Electron Microscopy (TEM) images of untreated, unstimulated platelets (FIG. 4A), untreated, collagen-stimulated platelets (FIG. 4B), LFM-A13 treated, collagen-stimulated platelets (FIG. 4C), and a graph of serotonin release from the platelets (FIG. 4D).

FIG. 6A is a composite concentration-effect curve of LFM-A13, showing the dose-dependent inhibition of collagen-induced platelet aggregation by LFM-A13.

FIGS. 6B and 6C are aggregation curves of platelets treated with LFM-A13 and then stimulated with collagen (FIG. 6B) or thrombin (FIG. 6C).

FIGS. 7A-7C show pharmacokinetic parameters of LFM-A13 in mice (FIG. 7A) and plasma concentration-time curves for LFM-A13 following i.p. versus i.v. injections of 25 mg/kg bolus (FIG. 7B) or 25 mg/kg versus 50 mg/kg i.p. injection (FIG. 7C).

FIGS. 8A-8H are histopathologic tissue sections from mice after thromboplastin-induced fatal thromboembolism, showing acute fibrin thrombi in pulmonary blood vessels and capillaries (FIGS. 8A, 8B), acute fibrin thrombi enmeshed with erythrocytes in pulmonary blood vessels (FIGS. 8C, 8D) and portal veins (FIGS. 8E, 8F), and acute platelet thrombi with little fibrin in a central vein (FIGS. 8G, 8H).

FIG. 9A shows cumulative proportions of mice surviving event-free according to the time after injection of thromboplastin, and FIG. 9B is a life-table analysis and statistical comparison.

DETAILED DESCRIPTION

Figure 1A:
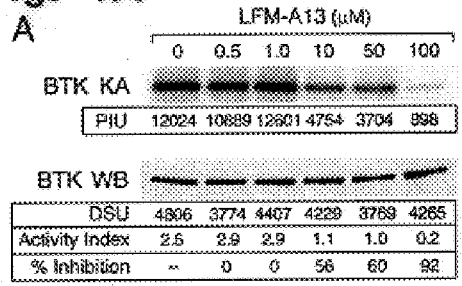
FIGS. 1A-1D show LFM-A13 prevents collagen-induced stimulation of BTK and TEC kinases in platelets, in kinase assays (upper panels) and Western blots (lower panels).

The present invention may be understood more readily by reference to the following detailed description of preferred embodiments of the invention, examples, and figures and their description.

In this specification and in the claims that follow, reference will be made to a number of terms that shall be defined to have the following meanings.

Reference in the specification and concluding claims to parts by weight of a particular component in a composition, denotes the weight relationship between the component and any other components in the composition for which a part by weight is expressed.

By "platelet aggregation" is meant the clumping together of platelets or red blood cells. As used herein, "inhibiting platelet aggregation" includes slowing platelet aggregation, as well as completely eliminating and/or preventing platelet aggregation. Additionally, "inhibiting platelet function" includes decreasing platelet function, as well as completely eliminating and/or preventing the platelet function.

As used herein, "treating a disease or condition" involving platelet aggregation includes decreasing the amount of platelet aggregation and/or slowing platelet aggregation, as well as completely eliminating and/or preventing platelet aggregation.

Conditions involving platelet aggregation include, but are not limited to, embolus formation, thrombolytic complications, thrombosis, coronary heart disease, thromboembolic complications, myocardial infarction, restenosis, and atrial thrombosis formation in atrial fibrillation, chronic unstable angina, transient ischemic attacks and strokes, peripheral vascular disease, arterial thrombosis, preeclampsia, embolism, restenosis and/or thrombosis following angioplasty, carotid endarterectomy, anastomosis of vascular grafts, and chronic exposure to cardiovascular devices. Such conditions may also result from thromboembolism and re-occlusion during and after thrombolytic therapy, after angioplasty, and after coronary artery bypass.

"Thrombin induced platelet aggregation" includes platelet aggregation in response to the enzyme thrombin that is formed in blood from prothrombin.

"Collagen induced platelet aggregation" includes platelet aggregation in response to the protein collagen.

As used throughout, by "contacting" is meant an instance of exposure of at least one cell (e.g., a neural cell, a stem cell, a cardiac cell) to an agent (e.g., a compound that inhibits platelet aggregation and specifically, collagen induced platelet aggregation).

The term "subject" is meant an individual. Preferably, the subject is a mammal such as a primate, and more preferably, a human. Thus, the "subject" can include domesticated animals (e.g., cats, dogs, etc.), livestock (e.g., cattle, horses, pigs, sheep, goats, etc.), and laboratory animals (e.g., mouse, rabbit, rat, guinea pig, etc.).

In general, "therapeutically effective amount", "therapeutically effective dose" and "effective amount" mean the amount needed to achieve the desired result or results (treating or preventing platelet aggregation). One of ordinary skill in the art will recognize that the potency and, therefore, an "effective amount" can vary for the various compounds that inhibit platelet aggregation and specifically, for inhibiting collagen induced platelet aggregation. Additionally, the "effective amount" of a compound may vary depending on the desired result, for example, the level of platelet aggregation inhibition desired. The "therapeutically effective amount" necessary for inhibiting platelet aggregation may differ from the "therapeutically effective amount" necessary for preventing platelet aggregation.

Additionally, an "embolism-inhibiting amount" of a compound may differ from an "thrombosis-inhibiting amount". One skilled in the art can readily assess the potency of the compounds.

By "pharmaceutically acceptable" is meant a material that is not biologically or otherwise undesirable, i.e., the material may be administered to an individual along with the selected bicyclic compound without causing any undesirable biological effects or interacting in a deleterious manner with any of the other components of the pharmaceutical composition in which it is contained.

A preferred compound for use in the present invention is α-cyano-β-hydroxy-β-methyl-N-(2,5-dibromophenyl)-propenamide (LFM-A13), and is structurally shown below (formula I):

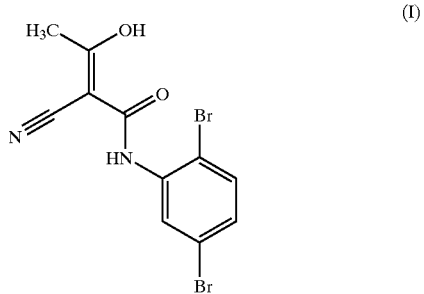

or a pharmaceutically acceptable salt thereof.

Characterization data of α-cyano-β-hydroxy-β-methyl-N-(2,5-dibromophenyl)-propenamide (LFM-A13) is as follows: mp: 148-150° C.; IR (KBr): 3353, 2211, 1648 and 1590 cm$^{-1}$; $^1$H NMR (DMSO-d$_6$):δ11.41 (s, 1H, NH), 8.57 (d, J=2.4 Hz, 1H, ArH), 7.55 (d, J=8.7 Hz, 1H, ArH), 7.14 (dd, J=8.7, 2.4 Hz, 1H, ArH), 7.10 (s br, 1H, OH), 2.17 (s, 3H, CH$_3$); MS (EI) m/z 362 (M$^+$+4), 360 (M$^+$+2), 358 (M$^+$), 253, 251, 249, 150.

Pharmaceutically acceptable salts of α-cyano-β-hydroxy-β-methyl-N-(2,5-dibromophenyl)-propenamide (LFM-A13), or any other compound useful in the present invention, may be used in the present invention. Examples of acceptable salts are organic acid addition salts formed with acids that form a physiological acceptable anion, including, but not limited to, tosylate, methanesulfonate, acetate, citrate, malonate, tartarate, succinate, benzoate, ascorbate, α-ketoglutarate, and α-glycerophosphate. Suitable inorganic salts may also be formed, including, but not limited to, hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion.

The compound of the present invention is readily synthesized using techniques generally known to synthetic organic chemists. Suitable experimental methods for making and derivatizing the compound is described in PCT Published Application No. WO99/54286 to Uckun et al., the disclosure of which is hereby incorporated by reference.

At low micromolar concentration, LFM-A13 inhibits collagen-induced BTK/TEC stimulation and BTK/TEC-dependent downstream signaling events, including tyrosine phosphorylation of PLCγ2 activation of phosphoinositide turnover with increased Ins-1,4,5-P$_3$ production, and degranulation/serotonin release. Following collagen stimulation, LFM-A13-treated platelets do not undergo shape changes indicative of activation, such as pseudopod formation. LFM-A13 inhibits collagen-induced platelet aggregation, but it does not affect thrombin-induced aggregation.

LFM-A13 was not toxic to mice when administered systemically at dose levels ranging from 1 mg/kg to 100 mg/kg. Highly effective platelet inhibitory plasma concentrations (≧10 μM) of LFM-A13 can be achieved in mice without toxicity. LFM-A13 prolonged the bleeding time of mice in a dose-dependent manner and markedly improved event-free survival in a mouse model of thromboplastin-induced generalized and fatal thromboembolism, involving the lungs, liver, heart, and CNS.

LFM-A13 is an anti-platelet agent targeting BTK and TEC kinases for prevention of potentially fatal thromboembolic events. The B-cell inhibitory effects of LFM-A13 may prove particularly useful in patients requiring long-term heparin therapy who are at risk for developing anti-heparin antibodies. Additionally, LFM-A13 may be useful in leukemia patients who are at risk to suffer thromboembolic complications because of their chemotherapy (e.g. L-Asparaginase)-induced hypercoagulable state.

Utility and Administration

The therapeutic method included herewith is useful for treating or preventing a condition involving or caused by platelet aggregation in a subject comprising administering to the subject a pharmaceutically effective amount of a compound or composition that inhibits BTK and that inhibits platelet aggregation, specifically, collagen induced platelet aggregation. Such platelet aggregation inhibition may selectively target the collagen pathway over other pathways including thrombin induced platelet aggregation.

The conditions involving or caused by platelet aggregation includes cardiovascular, hematopoietic and cerebrovascular diseases such as, but not limited to, embolus formation, thrombolytic complications, thrombosis, coronary heart disease, thromboembolic complications, myocardial infarction, restenosis, or atrial thrombosis formation in atrial fibrillation.

The methods include contacting the cells with such compounds or compositions, or administering to the subject a therapeutically effective amount of these compounds or compositions. In one embodiment, the cells are part of the blood and immune system including: red blood cell, megakaryocytes, macrophages (e.g. monocytes, connective tissue macrophages, Langerhans cells, osteoclasts, dendritic cells, microglial cells), neutrophils, eosinophils, basophils, mast cells, T lymphocytes (e.g. helper T cells, suppressor T cells, killer T cells), B lymphocytes (e.g. IgM, IgG, IgA, IgE), killer cell, and stem cells and committed progenitors for the blood and immune system. In another embodiment, the cells are contractile cells such as skeletal muscle cells (e.g. red, white, intermediate, muscle spindle, satellite cells), heart muscle cells (e.g. ordinary, nodal, Purkinje fiber), smooth muscle cells, and myoepithelial cells.

It is well known in the art how to determine the inhibition of platelet aggregation using the standard tests described herein, or using other similar tests. The method can result in at least a 10% reduction in collagen-induced platelet aggregation, including, for example, 15%, 20%, 25%, 30%, 40%, 50%, 60%, 70%, 80%, 90%, 100%, or any amount in between, more preferably by 90%. Similarly, the method would result in at least a 10% reduction in collagen-induced intracellular calcium mobilization including, for example, 15%, 20%, 25%, 30%, 40%, 50%, 60%, 70%, 80%, 90%, 100%. Similarly, the method would result in at least a 10% reduction in the level of phosphorylated PLCγ2 including, for example, 15%, 20%, 25%, 30%, 40%, 50%, 60%, 70%, 80%, 90%, 100%.

The reduction can be measured, for example, by comparing the optical impedance in a chronology platelet aggregometer. Any other known measurement method may also be used. For example, (1) upon collagen stimulation, the level of collagen-induced intracellular calcium mobilization increases over time and so the measurement may include measuring the level of collagen-induced intracellular calcium or (2) upon collagen stimulation, the level of phosphorylated PLCγ2 increases over time and so the measurement may include measuring the level of phosphorylated PLCγ2.

The cells can be contacted in vitro, for example, by adding the compound to the culture medium (by continuous infusion, by bolus delivery, or by changing the medium to a medium that contains the agent) or by adding the agent to the extracellular fluid in vivo (by local delivery, systemic delivery, inhalation, intravenous injection, bolus delivery, or continuous infusion). The duration of "contact" with a cell or population of cells is determined by the time the compound is present at physiologically effective levels or at presumed physiologically effective levels in the medium or extracellular fluid bathing the cell or cells. The duration of contact can be 1-96 hours, and can be for 24 hours, but such time would vary based on the half-life of the compound and could be optimized by one skilled in the art using routine experimentation.

Pharmaceutical Formulations

The compound useful in the present invention can be formulated as pharmaceutical compositions and administered to a mammalian host, such as a human patient or a domestic animal in a variety of forms adapted to the chosen route of administration, i.e., orally or parenterally, by inhalation, intravenous, intramuscular, topical or subcutaneous routes.

The compound of the present invention can also be administered using gene therapy methods of delivery. See, e.g., U.S. Pat. No. 5,399,346, which is incorporated by reference in its entirety. Using a gene therapy method of delivery, primary cells transfected with the gene for the compound of the present invention can additionally be transfected with tissue specific promoters to target specific organs, tissue, grafts, tumors, or cells.

Thus, the present compound may be systemically administered, e.g., orally, in combination with a pharmaceutically acceptable vehicle such as an inert diluent or an assimilable edible carrier. The combination may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques that yield a powder of the active ingredient plus any additional desired ingredient present in the previously sterile-filtered solutions.

For topical administration, the present compound may be applied in pure form, i.e., when they are liquids. However, it will generally be desirable to administer them to the skin as compositions or formulations in combination with a dermatologically acceptable carrier that may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the present compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compound of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. Also the dosage of the compound varies depending on the target cell, tumor, tissue, graft, or organ.

In general, however, a suitable dose will be in the range of from about 0.5 to about 100 mg/kg, e.g., from about 10 to about 75 mg/kg of body weight per day, such as about 3 to about 50 mg per kilogram body weight of the recipient per day, preferably in the range of 6 to 90 mg/kg/day, most preferably in the range of 15 to 60 mg/kg/day.

The compound may conveniently be administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.0005 to about 300 $\mu$M, preferably, about 0.001 to about 100 $\mu$M, more preferably, about 1 to about 100 $\mu$M. This may be achieved, for example, by the intravenous injection of a concentration of the active ingredient, optionally in saline, or orally administered as a bolus. Desirable blood levels may be maintained by continuous infusion to provide about 0.0005-50.0 mg/kg/hr or by intermittent infusions containing about 0.004-150 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

The invention will now be illustrated by the following non-limiting Examples.

Experimental

The following examples are put forth so as to provide those of ordinary skill in the art with a complete disclosure and description of how the compounds, compositions, articles, devices, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. or is at ambient temperature, and pressure is at or near atmospheric.

EXAMPLE 1
Recombinant Baculovirus Construction, Protein Expression and Immunoprecipitation of Recombinant Proteins from Insect Cells Sf21 (1PLB-SF1-AE) cells derived from the ovarian tissue of the fall armyworm *Spodotera frugiperda* were obtained from Invitrogen and maintained at 26-28° C. in Grace's insect cell medium supplemented with 10% FBS and 1.0% antibiotic/antimycotic (GIBCO-BRL). Stock cells were maintained in suspension at 0.2-1.6×10$^6$/mL in 600 mL total culture volume in 1 L Bellco spinner flasks at 60-90 rpm. Cell viability was maintained at 95-100% as determined by trypan blue dye exclusion. Recombinant baculoviruses containing the murine BTK or TEC genes were constructed as described (Mahajan et al., 1999). In brief, the gene encoding BTK/TEC was excised from pBluescript SKII$^+$ vector (Stratagene) by digestion with BamHI and this fragment was then ligated into pFastBac1 (Gibco-BRL). The resulting vector, pFastBac1-BTK/TEC, was then used to generate the recombinant baculovirus by site-specific transposition in *E. coli* DH10Bac cells (Gibco-BRL) which harbor a baculovirus shuttle vector (bacmid), bMON14272. The resultant recombinant bacmid DNA was introduced into insect cells by transfection with the standard liposome-mediated method using Cellfectin reagent (Gibco-BRL). Four days later, cells were harvested, lysed (10 mM Tris pH 7.6, 100 mM NaCl, 1% Nonidet P-40, 10% glycerol, 50 mM NaF, 100 $\mu$M Na$_3$VO$_4$, 50 $\mu$g/mL phenylmethylsulfonyl fluoride, 10 $\mu$g/mL aprotonin, 10 $\mu$g/mL leupeptin), and the BTK/TEC kinases were immunoprecipitated from the lysates, as reported (Vassilev et al., 1999).

EXAMPLE 2
Immunoprecipitation and Western Blotting Analysis

Platelets were isolated from platelet rich plasma (PRP) purchased from the Memorial Blood Bank (Minneapolis, Minn.) as previously described (Asselin et al. 1997) and used at a concentration of 3×10$^9$ cells/mL in a modified Tyrode's buffer (137 mM NaCl, 2.7 mM KCl, 0.9 mM MgCl$_2$, 5.5 mM glucose, 3.3 mM NaH$_2$PO$_4$, 3.8 mM Hepes, pH 7.4). Platelets were incubated with indicated concentrations of LFM-A13 or vehicle (PBS supplemented with 1% DMSO) for 30 minutes at 37° C. Platelets were then stimulated at 37° C. with 2 μg/mL (or 10 μg/mL) collagen or 0.1 U/mL thrombin (Chronolog Inc., Philadelphia, Pa.). Stimulation was stopped and platelets were lysed at the indicated time points by adding ice cold 3x Triton X-100 lysis buffer (150 mM NaCl, 15 mM EGTA, 3% Triton X-100, 3% Sodium deoxycholate, 0.3% SDS, 3 mM PMSF, 3 mM $Na_3VO_4$, 60 μg/mL leupeptin, 60 μg/mL aprotinin, 50 mM Tris-HCl pH 7.4) and incubating for 1 hour on ice. Following removal of the membranous fraction by centrifugation (12,000xg, 30 min) the samples were subjected to immunoprecipitation utilizing antibodies raised against BTK (Santa Cruz Biotechnologies, Santa Cruz, Calif.), TEC (Upstate Biotechnology, Lake Placid, N.Y.) and $PLC_\gamma 2$ (Santa Cruz Biotechnologies, Santa Cruz, Calif.) (Vassilev et al., 1999). Immunoprecipitations, immune-complex protein kinase assays, and immunoblotting on PVDF membranes (Milipore, Bedford, Mass.) using the ECL chemiluminescence detection system (Amersham Life Sciences, Arlington Heights, Ill.) were conducted as described previously (Mahajan et al., 1999; Sudbeck et al., 1999; Uckun et al., 1996a; Uckun et al., 1996b).

For immunoblotting, antibodies against phosphotyrosine (Transduction Labs, Lexington, Ky.), BTK (Santa Cruz Biotechnologies, Santa Cruz, Calif.), TEC (Upstate Biotechnology, Lake Placid, N.Y.) and $PLC_\gamma 2$ (Santa Cruz Biotechnologies, Santa Cruz, Calif.) were used. Horse radish peroxidase-conjugated sheep anti-mouse, donkey anti-rabbit secondary antibodies were purchased from Transduction Laboratories (Lexington, Ky.). Horse radish peroxidase-conjugated sheep anti-goat antibodies were purchased from Santa Cruz (Santa Cruz, Calif.). Following electrophoresis, kinase gels were dried onto Whatman 3M filter paper and subjected to phosphoimaging on a Molecular Imager (Bio-Rad, Hercules, Calif.) as well as autoradiography on film. Similarly, all chemiluminescent BTK/TEC Western blots were subjected to three dimensional densitometric scanning using the Molecular Imager and Imaging Densitometer using the Molecular Analyst/Macintosh version 2.1 software following the specifications of the manufacturer (Bio-Rad).

Kinase assays were performed following a 1 hour exposure of the immunoprecipitated tyrosine kinases to LFM-A13 (FIGS. 1A-1D), as described in detail elsewhere (Mahajan et al., 1999; Sudbeck et al., 1999; Uckun et al., 1996a). The immunoprecipitates were subjected to Western blot analysis (FIGS. 1A-1D) as previously described (Mahajan et al., 1999). Antibodies raised against BTK and TEC utilized for immunoprecipitations and Western blot analysis were purchased from Santa Cruz (Santa Cruz, Calif.).

EXAMPLE 3
Analysis of Stimulation of Inositol Phospholipid Turnover

Figure 2A:
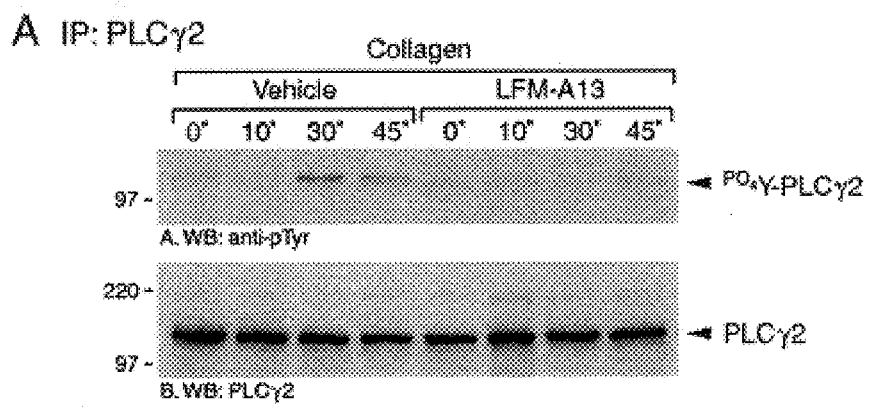
FIGS. 2A and 2B show LFM-A13 inhibition of collagen-induced activation of PLCγ2 and phosphoinositide turnover in platelets. Antibodies to phospho-tyrosine (FIG. 2A upper panel) and PLCγ2 (FIG. 2A lower panel) were used in Western blots. Ins-1,4,5-$P_3$ levels of platelets pretreated with LFM-A13 measured after collagen stimulation as shown in FIG. 2B.
Figure 2B:
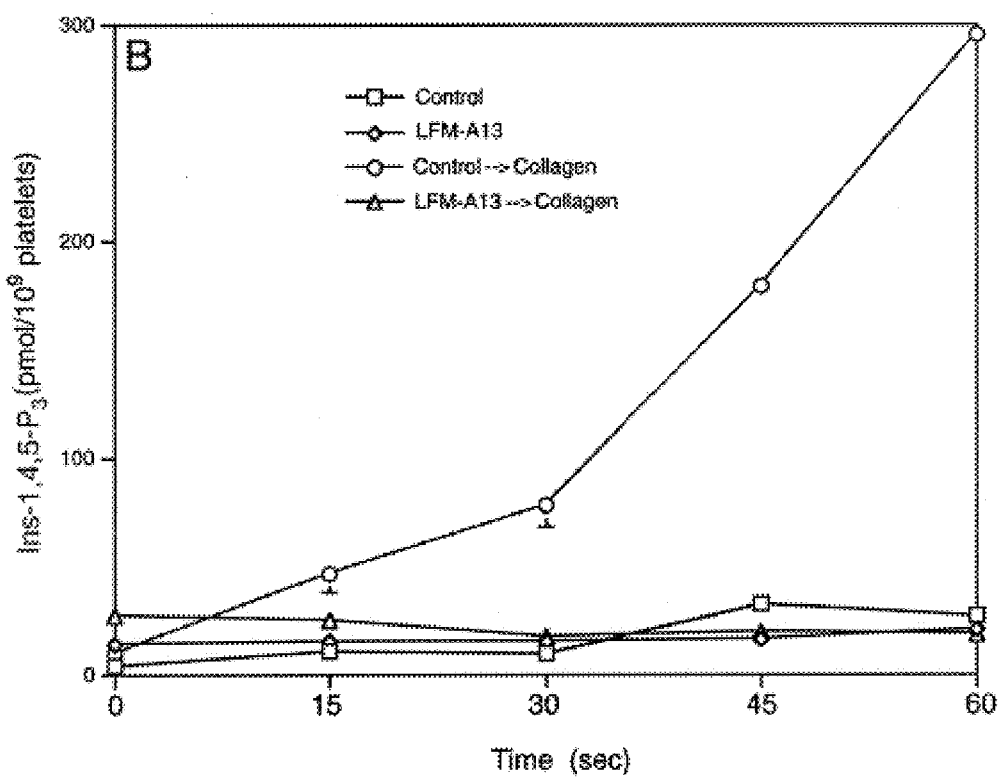

Platelets were incubated with 100 μM LFM-A13 or vehicle alone for 30 minutes at 37° C. Platelets were then stimulated at 37° C. with 2 μg/mL collagen or 0.1 U/mL thrombin for 0, 5, 10, 15, 30 and 60 seconds. Collagen stimulation was terminated by the addition of ice-cold 20% perchloric acid. Inositol-1,4,5,-trisphosphate (Ins-1,4,5-$P_3$) levels were measured by using a D-myo-[$^3$H]inositol-1,4,5-trisphosphate assay system purchased from Amersham (Arlington Heights, Ill.), as reported (Uckun et al., 1991) (FIG. 2B). This highly sensitive assay is based on the competition between nonradiolabeled Ins-1,4,5-$P_3$ in the cellular extracts and a fixed quantity of a high specific activity [$^3$H] Ins-1,4,5-$P_3$ tracer for a limited number of binding sites on a Ins-1,4,5-$P_3$-specific and sensitive bovine adrenal binding protein (Uckun et al., 1991).

For each drug concentration, a BTK/TEC kinase activity index as determined by comparing the ratios of the kinase activity in phosphorimager units (PIU) and density of the protein bands in densitometric scanning units (DSU) to those of the baseline sample and using the formula: Activity Index=[PIU of kinase band/DSU of BTK/TEC protein band]$_{test\ sample}$: [PIU of kinase band/DSU of BTK/TEC protein band]$_{baseline\ control\ sample}$ (FIGS. 1A-1D).

EXAMPLE 4
LFM-A13 Prevents Collagen-Induced Stimulation of BTK and TEC Kinases in Platelets.

Figure 1B:
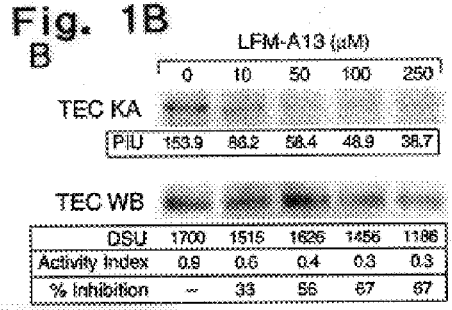
Figure 1C:
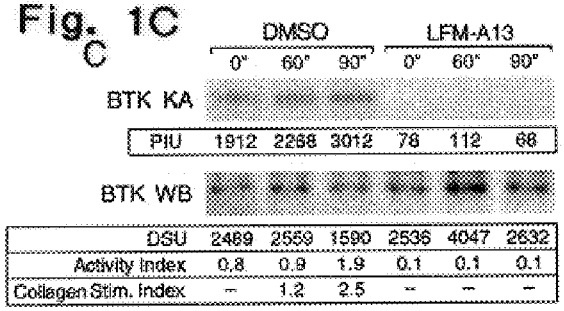
Figure 1D:
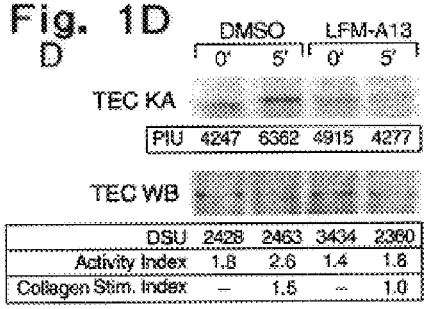

The leflunomide metabolite analog α-cyano-β-hydroxy-β-methyl-N-(2,5-dibromophenyl)-propenamide (LFM-A13) is a potent ($IC_{50}$ against purified recombinant BTK=2.5 μM) and specific inhibitor of the TEC family tyrosine kinase BTK ((Mahajan et al., 1999) and FIG. 1A). In cell-free immune complex kinase assays, LFM-A13 also inhibited recombinant TEC kinase expressed in a baculovirus vector expression system with an $IC_{50}$ value of 14.7 μM, (FIG. 1B). As shown in FIG. 1C, treatment of platelets with 2 μg/mL collagen rapidly stimulated the enzymatic activity of BTK with a maximum stimulation index of 2.5 at 90 seconds, as measured by quantitative immune complex kinase assays. Notably, treatment of platelets with LFM-A13 (100 μM) for 30 min at 37° C. reduced the baseline BTK activity by >90% and completely prevented collagen-induced stimulation of BTK (FIG. 1C). Similarly, LFM-A13 also prevented collagen-induced stimulation of TEC kinase in platelets but it did not reduce the baseline activity of TEC in unstimulated platelets (FIG. 1D). In accordance with its previously reported selectivity and lack of inhibitory activity on SYK and SRC-family tyrosine kinases (Mahajan et al., 1999), LFM-A13 did not inhibit the baseline activity of SYK or SRC or prevent collagen-induced SYK and SRC activation in platelets (data not shown).

EXAMPLE 5
LFM-A13 Inhibits BTK/TEC-Dependent Downstream Signaling Events in Collagen-Stimulated Platelets.

Stimulation of platelets with collagen (2 μm/mL) resulted in enhanced tyrosine phosphorylation of PLCγ2 (FIG. 2A) and increased Ins-1,4,5-$P_3$ production (FIG. 2B) within 30 seconds. At 30 seconds, the Ins-1,4,5-$P_3$ levels were 10.4±1.4 pmols/$10^9$ platelets in vehicle treated, unstimulated controls and 79.2±10.0 pmols/$10^9$ platelets in vehicle treated, collagen-stimulated test samples (P=0.007). Pretreatment of platelets with LFM-A13 (100 μM, 30 minutes) abrogated each of these BTK/TEC-dependent biochemical signaling events (FIGS. 2A & 2B). At 30 seconds after collagen stimulation, no enhanced tyrosine phosphorylation of PLCγ2 was detected in LFM-A13 pretreated platelets (FIG. 2A) and the Ins-1,4,5-$P_3$ levels of LFM-A13 pretreated, collagen-stimulated platelets were significantly lower than those of vehicle treated, collagen-stimulated control platelets (17.8±1.4 pmols/$10^9$ platelets versus 79.2±10.0 pmols/$10^9$ platelets, P=0.009) (FIG. 2B). While the Ins-1,4,5-$P_3$ levels of control platelets continued to increase between 30" and 60" after collagen stimulation, the Ins-1,4,5-$P_3$ levels of LFM-A13 pretreated platelets remained at baseline (FIG. 2B).

EXAMPLE 6
LFM-A13 Inhibits Collagen-Induced Activation and Degranulation of Platelets
High-Resolution Low-Voltage Scanning Electron Microscopy (HR-LVSEM)

HR-LVSEM was utilized for topographical imaging of the platelet surface membrane, as previously reported (D'Cruz et al., 1998). Aliquots of human platelets were incubated with 100 μM LFM-A13 or vehicle alone for 30 minutes. Treated platelets were then stimulated with collagen (10 μg/mL) or thrombin (0.1 U/mL) for 10 seconds (FIGS. 3A-3F). 3% glutaraldehyde was added to stop the reaction. Samples were prepared for HR-LVSEM as previously described (D'Cruz et al., 1998) and analyzed using a Hitachi S-900 SEM instrument (Hitachi Instruments, Gaithersburg, Md.) at an accelerating voltage of 2 kV and 40× magnification.

Figure 3A:
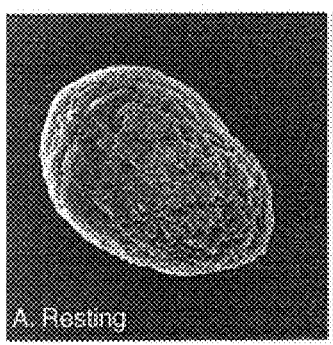
FIGS. 3A-3F are High-Resolution Low-Voltage Scanning Electron Microscopy (HR-LVSEM) images of platelet surface membrane in resting platelets (FIGS. 3A, 3B), control platelets stimulated with collagen (FIG. 3C), control platelets stimulated with thrombin (FIG. 3D), LFM-A13 pretreated platelets stimulated with collagen (FIG. 3E), and LFM-A13 pretreated platelets stimulated with thrombin (FIG. 3F).
Figure 3B:
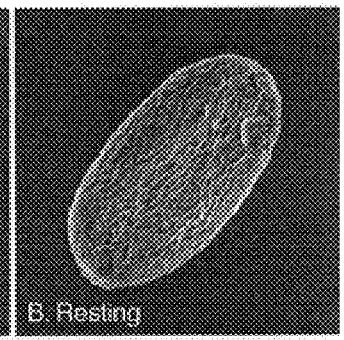
Figure 3C:
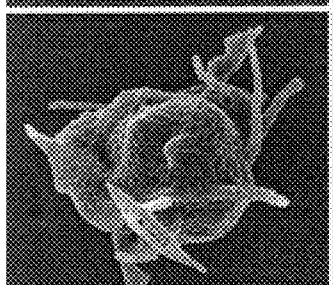
Figure 3D:
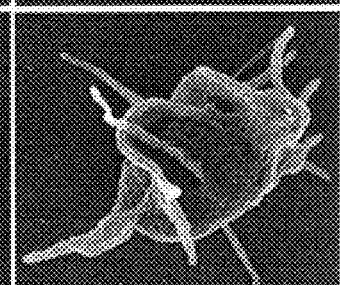
Figure 3E:
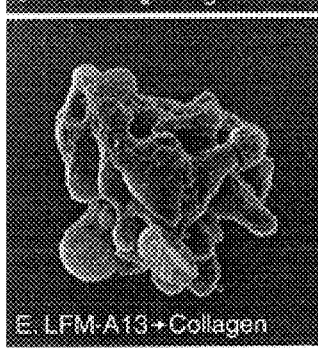
Figure 3F:
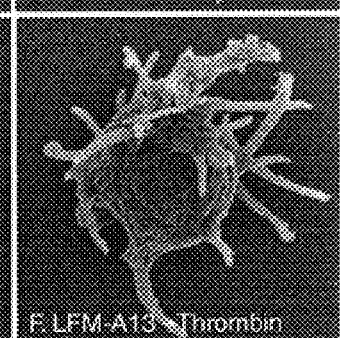

Platelet activation after collagen stimulation was accompanied by marked changes in platelet shape and ultrastructural organization. Topographical imaging showed induction of membrane ruffling and development of pseudopodious extensions indicative of activation (FIGS. 3C, 3E). Similar changes were observed after thrombin (0.1 U/mL) stimulation of platelets (FIGS. 3D, 3F). LFM-A13 (100 μM) inhibited collagen-induced pseudopod formation (FIG. 3E), but it did not inhibit the thrombin-induced shape changes (FIG. 3F).

Transmission Electron Microscopy (TEM)

Aliquots of human platelets were incubated with 100 μM LFM-A13 or vehicle alone for 30 minutes and then stimulated with collagen (10 μg/mL) for 10 seconds. Samples were then prepared for TEM as previously described (White, 1983). Briefly, 0.1% glutaraldehyde was added to stop the reaction. Following a brief centrifugation, the sample pellets were layered with 3% glutaraldehyde for 40 minutes at room temperature. The samples were then postfixed in 1% $OsO_4$ for 1 hour at 4° C., rinsed three times in distilled water at room temperature, dehydrated in a graded ethanol series (25, 50, 75, 90, 95 and 100%) and 100% propylene oxide. The samples were embedded in Embed 812 (Electron Microscopy Science, Washington, Pa.). Silver sections were picked up on mesh grids, stained 10 minutes in 1% uranyle acetate/70% ethanol, and 10 minutes in Reynold's lead citrate. Sections were viewed in a JEOL 100× electron microscope at 60 kV (FIGS. 4A-4C). True magnifications were determined by photographing a calibration grid at each magnification step on the microscope and using this scale to determine final print enlargements.

Examination of collagen-stimulated platelets by TEM at 40,000× magnification showed a rapid change from resting platelets with a discoid appearance and disperse distribution of granules (FIG. 4A) to spheres with pseudopods extending from the surface and coalescence of granules as well as canalicular cisternae in the center of the platelet as a prelude to degranulation (FIG. 4B). In contrast, no pseudopods were observed and the granules remained uniformly dispersed after collagen stimulation of LFM-A13-treated platelets (FIG. 4C). In accordance with its inhibitory effects on activation-associated shape changes and granule migration in collagen-stimulated platelets, LFM-A13 inhibited platelet degranulation after collagen stimulation, as evidenced by a markedly reduced amount of serotonin secreted from LFM-A13-treated platelets after collagen challenge (FIG. 4D).

EXAMPLE 7

LFM-A13 Inhibits Collagen-Induced Aggregation of Platelets

The effects of LFM-A13 on collagen-induced or thrombin-induced platelet aggregation in vitro were determined. Platelets treated with concentrations of LFM-A13 varying from 0.1 μM to 1000 μM or vehicle (1% DMSO in phosphate-buffered saline) were stimulated with 2 μg/mL or 5 μg/mL collagen or 0.1 U/mL thrombin. Platelet aggregation with respect to control was monitored in a Chronolog Model 560 Dual Chamber Platelet Aggregometer. Results are expressed as the percent control of collagen- or thrombin-induced maximum platelet aggregation as a function of the applied LFM-A13 concentration. LFM-A13 significantly reduced the platelet response to 2 μg/ml collagen with an $IC_{50}$ value of 2.78 μM and the platelet response to 5 μg/ml collagen with an $IC_{50}$ value of 66.1 μM. No significant effect was noted on the thrombin-induced platelet aggregatory response. The results are charted in FIG. 6A.

Figure 6A:
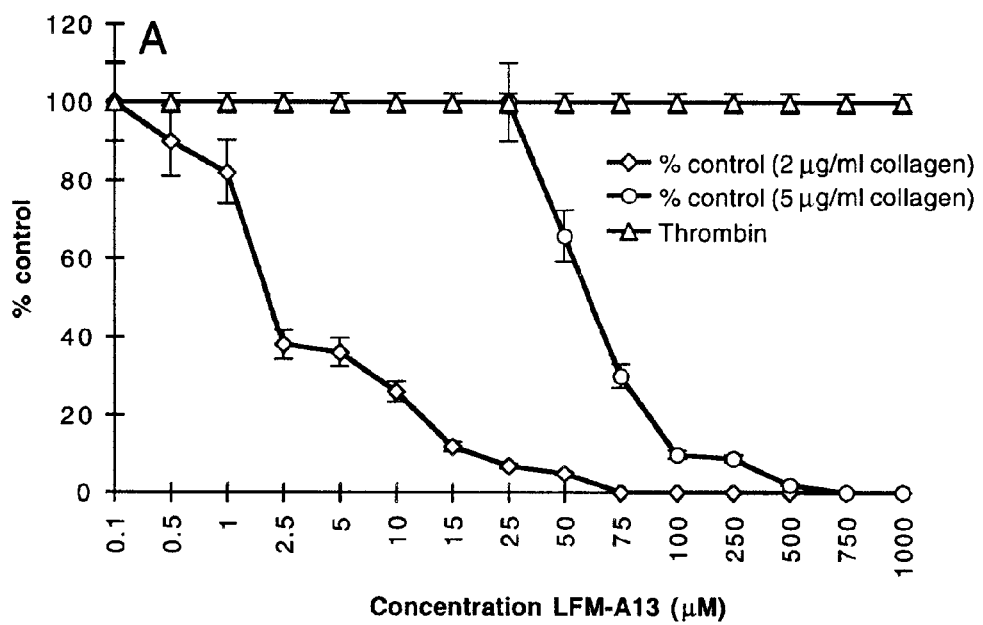
FIGS. 6A-6C are graphs showing the effects of LFM-A13 on collagen-induced versus thrombin-induced platelet aggregation.

Pretreatment of platelets with LFM-A13 for 30 minutes inhibited collagen-induced platelet aggregation in a concentration-dependent fashion. The average (mean±SE) $IC_{50}$ values for LFM-A13-mediated inhibition of agonist-iduced platelet aggregation were calculated by non-linear regression analysis. The values were 2.8±0.93 μM for inhibition of the aggregatory response to 2 μg/mL collagen and 66.1±5.3 μM for inhibition of the aggregatory response to 5 μg/mL collagen (FIG. 6A).

Figure 6B:
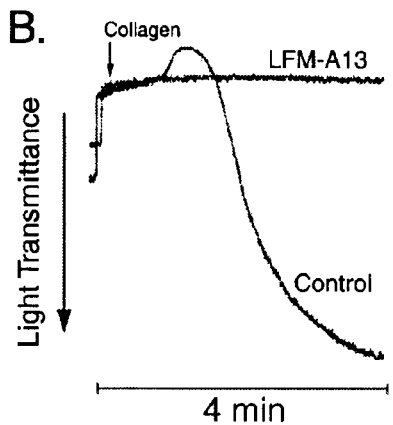
Figure 6C:
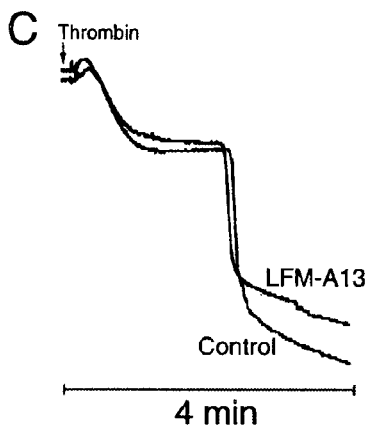

Representative traces of aggregation curves are shown in FIGS. 6B and 6C. A 30 minute pretreatment with 100 μM LFM-A13 completely prevented collagen-induced (2 μg/mL) platelet aggregation (FIG. 6B). The control is vehicle alone with collagen stimulation. In contrast to the marked inhibition of the collagen-induced platelet aggregation by LFM-A13, thrombin-induced (0.1 U/mL) platelet aggregation was not impaired by LFM-A13 at 100 μM (FIG. 6C) or even at 1000 μM (FIG. 6A).

Another set of PRP samples was treated with varying concentrations of LFM-A13 for 20 min or 24 hours at 37° C. Controls were treated with vehicle (PBS supplemented with 1% DMSO) alone. The treated PRP samples were diluted 1:4 with sterile normal saline and platelets were stimulated with collagen (2 μg/mL or 5 μg/mL, Chronolog Inc., Philadelphia, Pa.) or thrombin (0.1 U/mL, Chronolog Inc., Philadelphia, Pa.) as agonists under stirred conditions. Platelet aggregation was monitored in a platelet aggregometer (Model 560 Dual Chamber-Instrument, Chronolog Ind., Philadelphia, Pa.) for 5 minutes. The $IC_{50}$ values for LFM-A13-mediated inhibition of agonist-induced platelet aggregation were calculated by non-linear regression analysis using Graphpad Prism software version 2.0 (Graphpad Software, Inc., San Diego, Calif.). The results are shown in FIGS. 10A-10F.

Figure 10A:
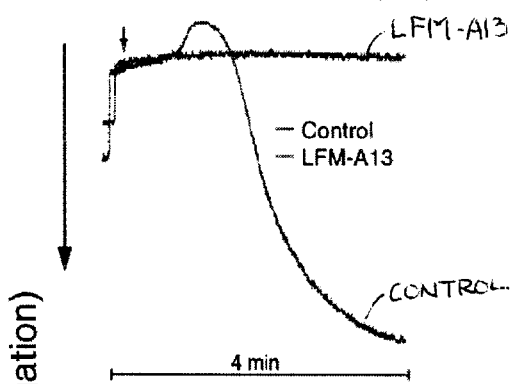
FIGS. 10A-10F are graphs showing experimental results for Example 7 including the platelet aggregation effects of collagen at 5 mg/mL for 20 minutes (FIG. 10A) and 24 hours (FIG. 10D) and collagen at 2 mg/mL for 20 minutes (FIG. 10B) and 24 hours (FIG. 10E), and thrombin for 20 minutes (FIG. 10C) and 24 hours (FIG. 10F).
Figure 10D:
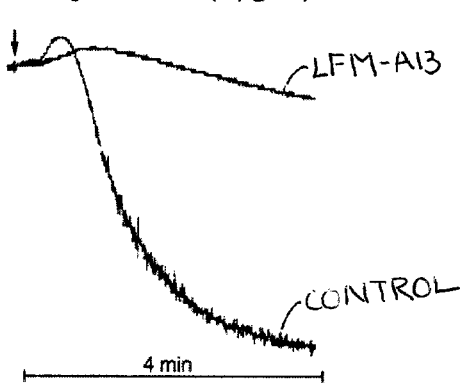
Figure 10B:
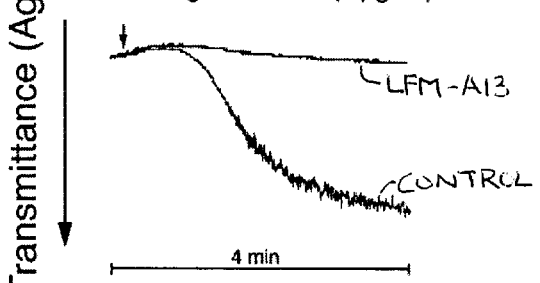
Figure 10E:
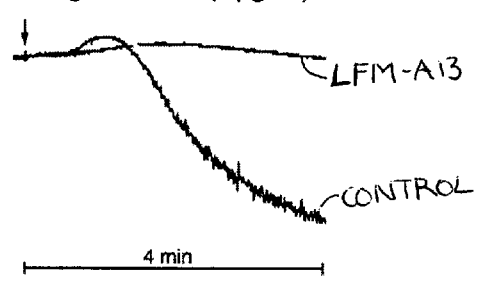
Figure 10C:
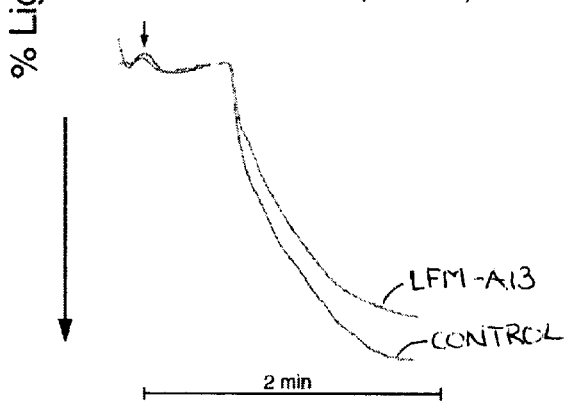
Figure 10F:
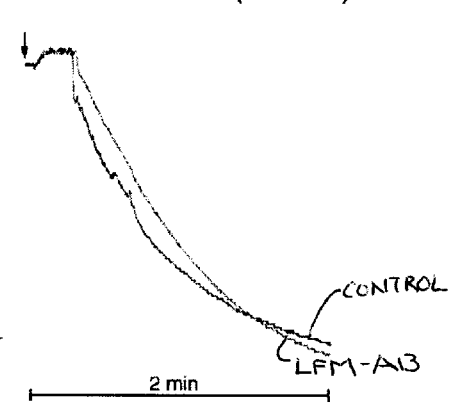

LFM-A13 significantly reduced the platelet response to high and low doses of collagen (as shown in FIGS. 10A, 10D and FIGS. 10B, 10E). No significant effect with LFM-A13 was noted on the thrombin-induced platelet aggregation (as shown in FIGS. 10C, 10F). Platelets treated with LFM-A13 for 24 hours responded in the same manner as those treated with the compound for 20 minutes.

EXAMPLE 8

Serotonin Release

Release of serotonin from collagen (10 and 20 μg/mL)-stimulated platelets was measured using a serotonin detection kit (Immunotech, Marseille, France) according to the manufacturer's specifications. Sonicated platelets were used for measurement of the total serotonin content of platelets. The measured serotonin values in platelet supernatants were 157±26 nM (N=4) for vehicle-treated control platelets, 930±191 nM for vehicle-treated, collagen stimulated platelets (N=4), and 369±14 nM (N=4) for LFM-A13 treated, collagen stimulated platelets (FIG. 4D).

EXAMPLE 9

Cytoskeletal Fractionation

Figure 5A:
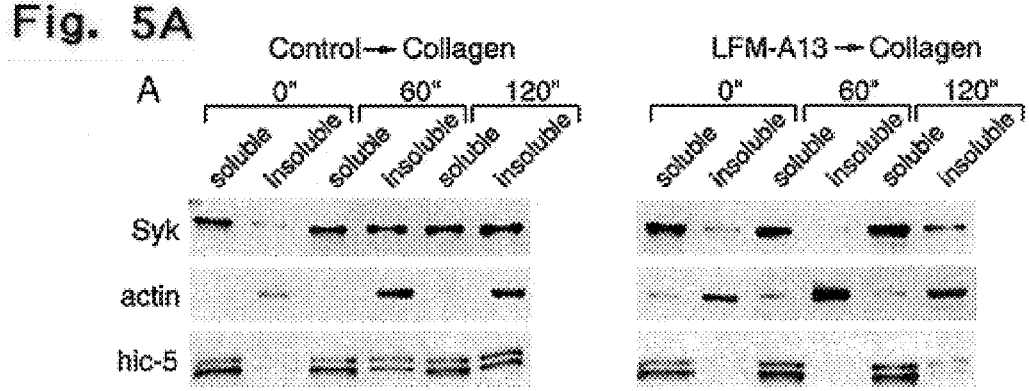
FIGS. 5A and 5B are Western blots of control (FIG. 5A) and LFM-A13 treated (FIG. 5B) platelets stimulated with thrombin or collagen and probed with antibodies to SYK, HIC-5 and actin.
Figure 5B:
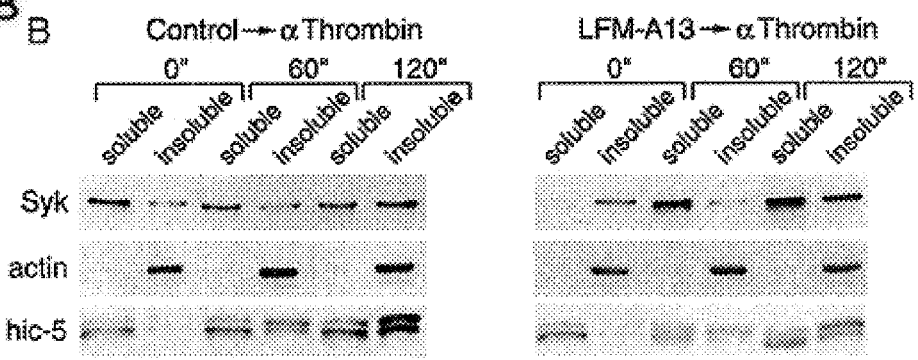

Platelets ($1\times10^8$/mL) were treated with LFM-A13 (100 μM, 30 min, 37° C.) or vehicle (1% DMSO) and stimulated with thrombin (0.1 U/mL) or collagen (10 μg/mL). Isolation of the TX-100 soluble and TX-100 insoluble cytoskeletal fractions was performed as previously described (Oda et al., 1992). Fractions were analyzed by Western blot analysis utilizing antibodies raised against SYK (Santa Cruz, Santa Cruz, Calif.), HIC-5 (Transduction Laboratories, Lexington, Ky.) and actin (Sigma, ST. Louis, Mo.) (FIGS. 5A-5B).

Activation and subsequent aggregation of platelets after exposure to collagen or thrombin is associated with actin polymerization and rapid translocation of the tyrosine SYK (Sada et al., 1997; Tohyama, 1994) as well as the paxillin-related LIM protein HIC-5 (Hagmann et al., 1998) to the TX-100 insoluble cytoskeletal fraction associated with the actin filament network. As shown in FIGS. 5A and 5B, Western blot analysis of the TX-100 soluble and TX-100 insoluble fractions from unstimulated platelets confirmed the presence of abundant amounts of actin in the insoluble fraction and SYK as well as HIC-5 proteins in the TX-100 soluble (but not insoluble) fraction. Within 60 seconds after collagen or thrombin (FIG. 5A) stimulation, a significant amount of SYK and HIC-5 translocated to the TX-100 insoluble fraction, as evidenced by the Western blot detection of SYK and HIC-5 in the actin-containing fractions. Notably, LFM-A13 inhibited collagen-induced (but not thrombin-induced) relocalization of SYK and HIC-5 in platelets (FIG. 5B).

EXAMPLE 10
Toxicity and Pharmacokinetics of LFM-A13 in Mice

Mice were housed in microisolator cages (Lab Products, Inc., Maywood, N.Y.) in a controlled USDA-accredited environment (12-h light/12-h dark photoperiod, 22±1° C., 60±10% relative humidity) under specific pathogen-free conditions. Mice were allowed free access to autoclaved standard pellet food and tap water. Animal studies were approved by the Parker Hughes Institute Animal Care and USE Committee and all animal care procedures conformed to the NIH Principles of Laboratory Animal Care. The toxicity profile of LFM-A13 in mice was examined, as previously reported for the JAK3 inhibitor WHI-P131 (Uckun et al., 1999). In brief, mice were administered an intraperitoneal (i.p.) bolus injection of LFM-A13 in 0.2 mL PBS supplemented with 10% DMSO, or 0.2 mL PBS supplemented with 10% DMSO alone (control mice). No sedation or anesthesia was used throughout the treatment period. Mice were monitored daily for mortality for determination of the day 30 $LD_{50}$ values. Mice surviving until the end of the 30 day monitoring were sacrificed, and several tissues (bone, bone marrow, brain, cecum, heart, kidney, large intestine, liver, lung, lymph node, ovary, pancreas, skeletal muscle, skin, small intestine, spleen, stomach, thymus, thyroid gland, urinary bladder, and uterus, as available) were immediately collected for histopathologic examination. For histopathologic studies, tissues were fixed in 10% neutral buffered formalin, dehydrated, and embedded in paraffin by routine methods. Glass slides with affixed 6 micron tissue sections were prepared and stained with Hemotoxylin and Eosin (H&E).

A study was done to determine whether highly effective platelet inhibitory plasma concentrations ($\geq 10$ μM) of LFM-A13 can be achieved in mice without toxicity by examining its pharmacokinetics in mice at 5 different non-toxic dose levels ranging from 10 mg/kg to 50 mg/kg administered i.p. and at a 25 mg/kg dose level administered i.v.

Mice were injected i.p. with 10 mg/kg, 20 mg/kg, 25 mg/kg, 40 mg/kg or 50 mg/kg or intravenously (i.v.) with 25 mg/kg LFM-A13 in vehicle (FIG. 7A). The mice were anaesthetized with methoxyflurane and 200 μL blood samples were obtained from the ocular plexus by retro-orbital venupuncture at 0, 3, 5, 10, 15, 30, and 45 minutes, and at 1, 1.5, 2, 4, and 6 hours after the i.p. administration of LFM-A13. All collected blood samples were heparinized and centrifuged at 7,000xg for 5 minutes in a microcentrifuge to obtain plasma. The plasma samples were stored at −20° C. until analysis. Aliquots of plasma were used for extraction and HPLC determination of plasma LFM-A13 levels (FIGS. 7B and 7C).

LFM-A13, when administered as a single i.p. bolus injection, was not toxic to mice (N=160) at dose levels ranging from 12.5 mg/kg to 100 mg/kg. None of the 40 mice treated with 100 mg/kg LFM-A13, 40 mice treated with 50 mg/kg LFM-A13, 40 mice treated with 25 mg/kg LFM-A13, or 40 mice treated with 12.5 mg/kg LFM-A13 showed any signs of toxicity (data not shown).

After administration of a single i.v. bolus dose of 25 mg/kg or i.p. bolus dose of 50 mg/kg in mice, LFM-A13 plasma concentrations of >10 μM, which substantially inhibited collagen responses of platelets in vitro, were achieved within 3 minutes and maintained for >2 h (FIGS. 7B and 7C).

EXAMPLE 11
Quantitative HPLC Determination of LFM-A13 Levels

For the quantitative HPLC determination of LFM-A13 levels, an acetonitrile/ammonium phosphate (10 mM, pH 3.7) buffer (35/65 v/v) was used as the mobile phase for the separation of the drug. The analytical column was equilibrated and eluted under isocratic conditions utilizing a flow rate of 1.0 mL/min at ambient temperature. The wavelength of detection was set at 294 nm. Peak width, response time, and slit were set at >0.03 min, 0.55 sec, and 4 mn, respectively. For extraction of LFM-A13 from plasma, 75 μL of methanol was added to each 25 μL plasma sample and the mixture was vortexed thoroughly for 1 minute. Following centrifugation at 300xg for 5 minutes, the supernatant was used for HPLC analysis using a system comprised of a Hewlett Packard (HP) series 1100 instrument equipped with an automated electronic degasser, a quaternary pump, an autosampler, an automatic thermostatic column compartment, diode array detector and a computer with a Chemstation software program for data analysis (Chen and Uckun, 1999; Malaviya et al., 2000). All extraction procedures were carried out at room temperature.

In order to generate a standard curve, LFM-A13 was added to plasma to yield final concentrations of 0.1, 0.2, 0.5, 1.0, 2.0, 5.0, 10, 20, 50, 100, 200, and 400 μM. The plasma samples with known amounts of LFM-A13 were extracted as described above and the standard curves were generated by plotting the peak area ratios against the drug concentrations tested. The unweighed linear regression analysis of the standard curves was performed by using the CA-Cricket Graph III computer program, Version 1.0 (Computer Association, Inc., Islandia, N.Y.). The linearity was confirmed using the Instat Program V.3.0 (GraphPad Software, San Diego, Calif., USA). Pharmacokinetic modeling and pharmacokinetic parameter estimations were carried out using the pharmacokinetics software, WinNonlin Program, Professional version 3.0 (Pharsight Inc., Mountain view, Calif.) (Chen and Uckun, 1999; Malaviya et al. 2000; Uckun et al., 1999).

The elimination half-life was estimated by linear regression analysis of the terminal phase of the plasma concentration time profile. The area under the concentration time curve (AUC) was calculated by the linear trapezoidal rule between the first (0 hours) and last sampling time plus C/k, where C is the concentration at the last sampling time and k is the elimination rate constant. The systemic clearance (CL)

was determined by dividing the does by the AUC (Chen and Uckun, 199; Malaviya et al., 2000; Uckun et al., 1999).

A one-compartment, first order pharmacokinetic model was fit into the pharmacokinetic data. The computer-fitted pharmacokinetic parameter values are shown in FIGS. 7A-7C. The numbers represent the average values estimated from the composite plasma concentration-time curve for pooled data. The mean±SEM values are indicated in parentheses. The values for the apparent volume of distribution (Vc) and systemic clearance (CL) were not corrected for bioavailability. $t_{1/2}$=terminal elimination half-life; $t_{max}$=the time required to reach the maximum plasma drug concentration after i.p. administration. The estimated values for AUC and $C_{max}$ after i.p. administration showed a linear relationship to the applied dose level. The observed dose-dependent decrease in systemic clearance indicates a saturable clearance mechanism, which contributes to the dose-dependent increases in $C_{max}$ and AUC after i.p. administration of LFM-A13 (FIG. 7A). The average AUC/$C_{max}$ values were 66.3±3 µM.h/94±8 µM at 10 mg/kg, 183±14 µM.h/243±16 µM at 20 mg/kg, 308±31 µM.h/383±35 µM at 25 mg/kg, 653±47 µM.h/640±44 µM at 40 mg/kg, and 1023±31 µM.h/940±16 µM at 50 mg/kg (FIG. 7A). The average AUC and $C_{max}$ values after the i.v. bolus dose of 25 mg/kg were 384±30 µM.h and 731±22 µM, respectively.

EXAMPLE 12
LFM-A13 Prolongs Bleeding Time

Mice were treated intravenously with 200 µL vehicle (PBS supplemented with 10% DMSO) or varying doses of LFM-A13 in 200 µL vehicle. Mice were placed in a tube holder and tail bleeding was performed with a 2 mm cut from the protruding tail tip, the tail was placed vertically into 10 mL normal saline in a 37° C. water bath and bleeding times determined as previously described (Teng et al., 1997). Platelet plug formation and clotting times on the eye after retro-orbital venupuncture were evaluated using published methods (Sheu et al., 1995).

As anticipated from its potent platelet inhibitory effects in vitro, LFM-A13 prolonged the bleeding time of mice in dose-dependent manner: the average tail bleeding times were 1.5±0.1 min for vehicle-treated controls (N=12), 7.4±1.0 min (4.9-fold prolongation, P<0.001) for 20 mg/kg LFM-A13 (N=5) 8.5±0.6 min (5.6-fold prolongation, P<0.001) for 40 mg/kg LFM-A13 (N=5), and 9.5±0.5 min (6.3-fold prolongation, P<0.001) for 80 mg/kg LFM-A13 (N=12) (Table 1). Similarly, 40 mg/kg LFM-A13 also delayed the local platelet plug ("eye plug") formation (45±4 sec versus 27±2 sec, P<0.001) and prolonged the clotting ("eye clot") time (2.6±0.4 min versus 1.6±0.2 min, P<0.05) after retroorbital venupuncture (Table 1).

EXAMPLE 13
LFM-A13 Protects Against Thromboplastin-Induced Fatal Thromboembolism in Mice at Non-Toxic Dose Levels 4-6 week old male ICR (International cancer Research) mice were treated intravenously with 200 µL of vehicle (PBS supplemented with 10% DMSO), varying doses of LFM-A13 in 200 µL of vehicle (administered i.p. 30 minutes prior to the thromboplastin challenge), or warfarin (3 mg/kg administered i.p. 18 hours prior to the thromboplastin challenge). The mice were challenged with 25 mg/kg thromboplastin (Sigma, St. Louis, Mo.) via a bolus i.v. injection in to the tail vein as previously described (Sato et al., 1998). At the time of thromboembolism-related death, after the thromboplastin injection or elective sacrifice at 48 hours using ketamine/xylazine, all mice were perfused with PBS followed by 4% phosphate buffered formalin. PBS and formalin were pumped through the left ventricle of the heart and allowed to exit through a 3 mm incision through the anterior wall of the right ventricle. During necropsy, several selected tissues (brain, heart, liver, lungs) were harvested, fixed in 10% neutral buffered formalin, dehydrated, and embedded in paraffin by routine methods for histopathologic examination. Glass slides with affixed 6 micron tissue sections were prepared and stained with hemotoxylin and eosin (H&E) or Masson's trichrome staining.

Notably, LFM-A13 markedly improved event-free survival (EFS) in a mouse model of thromboplastin-induced generalized and fatal thromboembolism. In this model, 100% of the challenged mice develop dyspnea, ataxia, and seizures and die within 10 minutes after the thromboplastin challenge from widespread thrombosis in multiple organs and massive pulmonary thromboembolism (FIGS. 8A-8H). Multiple acute fibrin thrombi are present in pulmonary blood vessels and capillaries (FIG. 8A=10× magnification; FIG. 8B=40× magnification). Acute fibrin thrombi enmeshed with erythrocytes are present in pulmonary blood vessels (box in FIG. 8C, 10× magnification; FIG. 8D=40× magnification). Multiple acute fibrin thrombi with enmeshed erythrocytes are present in liver portal veins (box in FIG. 8E, 10× magnification; FIG. 8F=40× magnification). Acute platelet thrombi with little fibrin present in a liver central vein is shown in FIGS. 8G and 8H, stained with Masson's Trichrome (FIG. 8G=10× magnification; FIG. 8H=40× magnification).

Figures 9A, 9B:
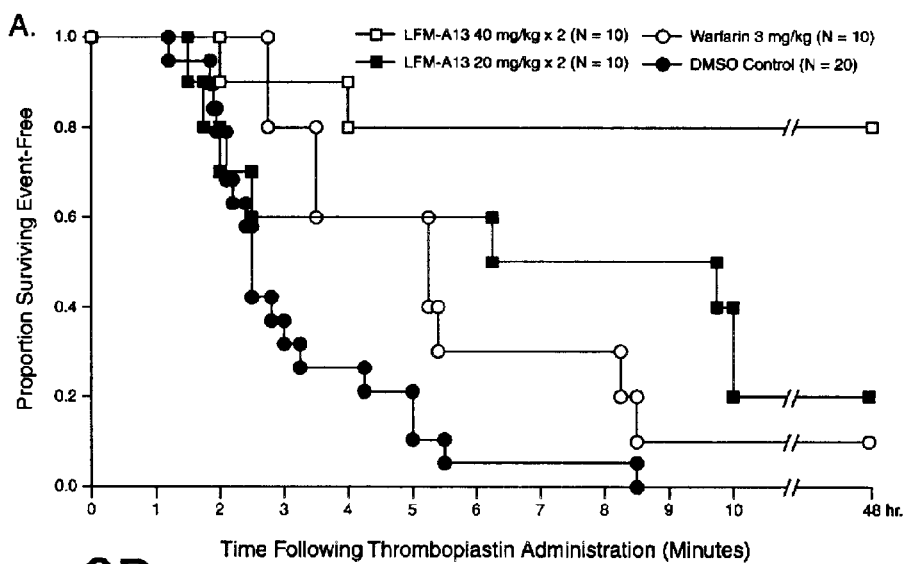
FIGS. 9A and 9B are graphs showing the protective effects of LFM-A13 in a mouse model of fatal thromboembolism.

The probability of EFS after the thromboplastin challenge was 0±0% (median survival time=2.5 min) for the vehicle-treated (200 µL vehicle) control group (N=20), 10±9% (median survival time=5.3 min) for the control group treated with the standard anti-coagulant drug warfarin at a 3 mg/kg dose level (N=10) (P=0.169), 20±13% (median survival time=8.0 min) for mice treated with LFM-A13 at the 20 mg/kg dose level (N=10) (P=0.044), and 80±13% (median survival time >48 hours) for mice treated with LFM-A13 at the 40 mg/kg dose level (N=10) (P=0.001). FIG. 9A show the cumulative proportions of mice surviving event-free according to the time after the injection of thromboplastin. FIG. 9B is a life-table analysis and statistical comparison using the log-rank test (Uckun et al. (1995) Science 267:886-891; Uckun et al. (1997) Blood 90:28-35; Uckun et al. (1998) J Clin Oncol 16:527-535). The cause of death in LFM-A13 pretreated, thromboplastin-challenged mice was generalized thromboembolism. No drug-related toxic lesions were detected in any of the organs of these mice.

EXAMPLE 14

Platelets were incubated with 100 µM LFM-A13 or DMSO for 30 minutes at 37 degrees C. and then stimulated with 2 µg/ml collagen. The samples were subjected to immunoprecipitation utilizing antibodies raised against BTK. The BTK immune complexes were subjected to immune kinase assays. Additional BTK immune complexes were collected, boiled in 2x SDS reducing sample buffer, fractionated on 8% polyacrylamide gels, transferred to PVDF membranes and examined for the presence of BTK by western blotting analysis. The enzymatic activity (activity index) of BTK was estimated by comparing the autophosphorylation (PIU) to the relative density of the protein bands in densitometric scanning units (DSU). The results are shown in Table 1 and indicate that LFM-A13 significantly inhibited BTK kinase activity.

TABLE 1

| Measurement | DMSO 0 seconds | DMSO 90 seconds | LFM-A13 0 seconds | LFM-A13 90 seconds |
|---|---|---|---|---|
| PIU | 1912 | 3012 | 78 | 68 |
| DSU | 2489 | 1590 | 1236 | 1432 |
| Activity | 0.77 | 1.89 | 0.17 | 0.05 |

EXAMPLE 15

Platelets were incubated with 100 μM LFM-A13 or DMSO for 30 minutes at 37 degrees C. and then stimulated with 2 μg/ml collagen. The samples were subjected to immunoprecipitation utilizing antibodies raised against PLCγ2 and immunoblotted against antibodies against phosphotyrosine. The membrane was stripped and re-probed with antibodies raised against PLCγ2. An increase in the level of phosphorylated PLCγ2 was seen between 30 and 45 seconds following collagen stimulation. No phosphorylation of PLCγ2 was noted with LFM-A13 treatment. Thus, LFM-A13 inhibited collagen induced PLCγ2 tyrosine phosphorylation.

EXAMPLE 16

Platelets were loaded with 3 mM fura-3 (Molecular Probes, Eugene Oreg.) for 15 minutes at 37 degrees C. Following a short wash (10 minutes, 3000 rpm), the platelets were resuspended in Hepes buffer ($1 \times 10^8$ cells/ml) and stimulated with collagen (20 μg/ml) in the presence or absence of 100 μM LFM-A13. The changes in fluorescence were monitored on a spectrofluorimeter. LFM-A13 significantly reduced (inhibited) collagen-induced calcium mobilization.

EXAMPLE 17

Platelets ($1 \times 10^9$) were incubated with and without 100 μM LFM-A13 for 30 minutes at 37 degrees C. Platelets were stimulated at 37 degrees C. with 2 μg/ml collagen for various times. Activation was stopped by the addition of ice cold 20% perchloric acid. The amount of inositol 1,4,5-triphosphate production was measured using a detection kit from Amersham. The results show that LFM-A13 inhibited collagen-stimulated PI-PLC activity. The results are shown in Table 2.

TABLE 2

| Treatment | % control inositol 1,4,5-triphosphate production (peak response) | Standard error | % inhibition |
|---|---|---|---|
| saline | 100 | 0 | — |
| LFM-A13 | 75 | 23 | — |
| collagen | 321 | 23 | — |
| collagen and LFM-A13 | 75 | 23 | 100 |

EXAMPLE 18

The clotting times of C57BL/6 mice both chronically (25 mg/kg/36 days) and acutely (40 mg/kg/1 hour) treated with LFM-A13 were compared with the clotting times of XID and control mice. The blood of XID mice clotted approximately two minutes later than the CBA control mice. Following this pattern, blood from chronically treated mice also clotted two minutes later than control. The results show that LFM-A13 decreases blood clotting time. Results are shown below in Table 3.

TABLE 3

| Mouse Type | Mean Clotting Time (min) n = 3 | Standard Error | % Control |
|---|---|---|---|
| CBA | 1.3 | 0.11 | — |
| XID | 3.2 | 0.27 | 246 |
| C57BL/6 DMSO control | 1.6 | 0.20 | — |
| C57BL/6 25 mg/kg chronic 36 days | 3.7 | 0.27 | 231 |
| C57BL/6 40 mg/kg acute 1 hour | 2.6 | 0.43 | 164 |

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method for inhibiting collagen-induced platelet aggregation in a subject comprising administering to the subject an effective amount of a compound of the formula:

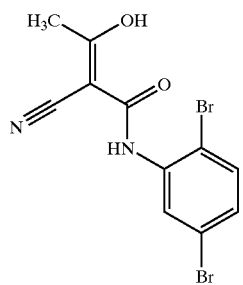

or a pharmaceutically acceptable acid addition salt thereof.

2. The method of claim 1, wherein the method specifically acts to inhibit collagen-induced platelet aggregation without significantly inhibiting thrombin-induced platelet aggregation.

3. A method of treating a disease or condition involving or caused by platelet aggregation in a subject comprising administering to the subject an effective amount of a compound of the formula:

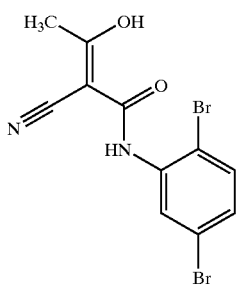

or a pharmaceutically acceptable acid addition salt thereof.

4. The method of claim 3, wherein the disease or condition comprises a cardiovascular, cerebrovascular, or hematologic disease at risk for thromboembolic complications.

5. The method of claim 4, wherein the condition involving platelet aggregation comprises embolus formation, thrombolytic complications, disseminated intravascular comgelopathy, thrombosis, coronary heart disease, thromboembolic complications, myocardial infarction, restenosis, or atrial thrombosis formation in atrial fibrillation.

6. The method of claim 3, wherein the disease or condition is an embolism.

7. The method of claim 6, wherein the amount of the compound administered to the subject is an embolism-inhibiting amount.

8. The method of claim 6, wherein the embolism comprises embolus formation, thrombolytic complications, thrombosis, thromboembolic complications, or atrial thrombosis.

9. The method of claim 6, wherein the embolism is a thromboembolism.

10. A method for inhibiting collagen-induced intracellular calcium mobilization, collagen-induced PLCγ2 production, or collagen-induced inositol 1,4,5-triphosphate production in a subject comprising administering to the subject an effective amount of a compound of the formula:

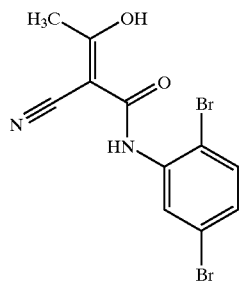

or a pharmaceutically acceptable acid addition salt thereof.

11. The method of claim 3, wherein the condition involving platelet aggregation is blood-clotting time, wherein the compound is administered in an amount effective to increase the blood-clotting time.

* * * * *

UNITED STATES PATENT AND TRADEMARK OFFICE
CERTIFICATE OF CORRECTION

PATENT NO.    : 6,589,992 B2
DATED         : March 18, 2003
INVENTOR(S)   : Fred P. Lampropoulos et al.

It is certified that error appears in the above-identified patent and that said Letters Patent is hereby corrected as shown below:

Column 6,
Line 67, change "11described" to -- described --.

Column 7,
Line 65, change "Espafiol" to -- Español --

Column 15,
Lines 20-21, change "U.S. letters patent" to -- United States Letters Patent --

Column 20,
Line 6, before "the" insert -- to --

Column 27,
Line 3, change "computer executable" to -- computer-executable --

Signed and Sealed this

Eighteenth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,589,992 B1
DATED         : March 18, 2003
INVENTOR(S)   : Fred P. Lampropoulos et al.

It is certified that error appears in the above-identified patent and that said Letters Patent is hereby corrected as shown below:

Column 6,
Line 67, change "11described" to -- described --

Column 7,
Line 65, change "Espafiol" to -- Español --

Column 15,
Lines 20-21, change "U.S. letters patent" to -- United States Letters Patent --

Column 20,
Line 6, before "the" insert -- to --

Column 27,
Line 3, change "computer executable" to -- computer-executable --

Signed and Sealed this

Thirteenth Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,589,992 B2
DATED : July 8, 2003
INVENTOR(S) : Faith M. Uckun

It is certified that error appears in the above-identified patent and that said Letters Patent is hereby corrected as shown below:

This certificate supersedes Certificate of Correction issued November 18, 2003, the number was erroneously mentioned and should be vacated since no Certificate of Correction was granted.

Signed and Sealed this

Twenty-fourth Day of August, 2004

JON W. DUDAS
*Director of the United States Patent and Trademark Office*